United States Patent
Singhal et al.

(10) Patent No.: US 12,020,495 B2
(45) Date of Patent: Jun. 25, 2024

(54) DEVICE AND A METHOD FOR LIGHTING, CONDITIONING AND CAPTURING IMAGE(S) OF ORGANIC SAMPLE(S)

(71) Applicant: AIRAMATRIX PRIVATE LIMITED, Thane-West (IN)

(72) Inventors: Nitin Singhal, Bangalore (IN); Bharathi Vijay, Thane West (IN); Satya Chaitanya Kondragunta, Mumbai (IN)

(73) Assignee: AIRAMATRIX PRIVATE LIMITED (IN)

( * ) Notice: Subject to any disclaimer, the term of this patent is extended or adjusted under 35 U.S.C. 154(b) by 312 days.

(21) Appl. No.: 17/515,924

(22) Filed: Nov. 1, 2021

(65) Prior Publication Data

US 2022/0138452 A1 May 5, 2022

(30) Foreign Application Priority Data

Nov. 2, 2020 (IN) .............................. 202021047692

(51) Int. Cl.
| | |
|---|---|
| G06V 20/69 | (2022.01) |
| G01N 15/10 | (2006.01) |
| G02B 5/02 | (2006.01) |
| G03B 15/03 | (2021.01) |
| G06V 10/141 | (2022.01) |

(Continued)

(52) U.S. Cl.
CPC ....... *G06V 20/693* (2022.01); *G01N 15/1023* (2024.01); *G02B 5/0278* (2013.01); *G03B 15/03* (2013.01); *G06V 10/141* (2022.01); *G06V 10/147* (2022.01); *G06V 20/698* (2022.01); *H04N 23/56* (2023.01); *H04N 23/64* (2023.01); *H04N 23/695* (2023.01); *G01N 2015/1024* (2024.01); *G06N 5/02* (2013.01)

(58) Field of Classification Search
CPC .. G06V 20/693; G06V 10/147; G06V 10/141; H04N 23/56; H04N 23/64
See application file for complete search history.

(56) References Cited

U.S. PATENT DOCUMENTS

| | | | | |
|---|---|---|---|---|
| 5,369,431 A | * | 11/1994 | Levy | G01R 31/2808 348/126 |
| 5,585,616 A | * | 12/1996 | Roxby | G06K 7/1092 250/208.6 |

(Continued)

*Primary Examiner* — Kathleen V Nguyen
(74) *Attorney, Agent, or Firm* — Edmonds & Cmaidalka, P.C.

(57) ABSTRACT

Micro-biological colony counters and more particularly, to a device and a method for lighting, conditioning and capturing image(s) of organic sample(s) such as but not limited to micro-organisms. The device (700) captures accurate image(s) of organic sample(s) and has a fixed focus imaging for repeatability in quality of images. The device (700) can capture images of organic sample in different lighting and color conditions thereby improving detection of microbiological colonies by increasing the contrast from the background medium. The color calibrated imaging device (700) provides diffused illumination by using polychromatic LED lights, light reflectors and light diffusers for optimal color reproduction of micro-biological colonies contained in organic sample(s). The device (700) is adapted for automatic capturing of images of organic sample(s) cultivated on petri dishes of different sizes.

7 Claims, 4 Drawing Sheets

(51) Int. Cl.
*G06V 10/147* (2022.01)
*H04N 23/56* (2023.01)
*H04N 23/60* (2023.01)
*H04N 23/695* (2023.01)
*G06N 5/02* (2023.01)

(56) References Cited

U.S. PATENT DOCUMENTS

| | | | | |
|---|---|---|---|---|
| 2003/0090659 | A1* | 5/2003 | Welchman | G01N 21/951 |
| | | | | 356/394 |
| 2015/0339510 | A1* | 11/2015 | Bolea | G06V 20/693 |
| | | | | 382/133 |
| 2016/0077407 | A1* | 3/2016 | Kubota | G03B 15/06 |
| | | | | 362/399 |
| 2019/0313024 | A1* | 10/2019 | Selinger | G08B 13/19636 |
| 2022/0360699 | A1* | 11/2022 | Anandasivam | G06V 10/17 |

* cited by examiner

DEVICE AND A METHOD FOR LIGHTING, CONDITIONING AND CAPTURING IMAGE(S) OF ORGANIC SAMPLE(S)

CROSS REFERENCE TO RELATED APPLICATION

This application is based on and derives the benefit of Indian Application 202021047692, filed Nov. 2, 2020, the contents of which are incorporated herein by reference.

TECHNICAL FIELD

The embodiments herein generally relate to a microbiological colony counters and more particularly, to a device and a method for lighting, conditioning and capturing image(s) of organic sample(s) such as but not limited to micro-organisms.

BACKGROUND

Microbiology is the study of microscopic organisms such as bacteria, algae, viruses, archaea, fungi and protozoa. Microbiology includes fundamental research on the biochemistry, physiology, cell biology, ecology, evolution and clinical aspects of the micro-organisms. Further, microbiology research includes the formation of colonies of micro-organisms such as bacteria on a growth medium such as agar which is disposed on a petri dish. The microbial colonies are manually counted by a lab technician using microscope devices, wherein the count of the individual colonies is used to determine the effectiveness of various chemicals. Such colony counting is performed in laboratory work, biomedical facilities and also in pharmaceutical industry. For example, the number of organisms in a blood agar may be counted in a research laboratory or a physician may make a culture of an infections organism during an examination. Further, in quality control of food and beverage industries, the number of micro-organisms present in a product must be regularly checked. Also, in pharma industry the number of micro-organisms in clean room setting must be checked regularly and in compliance with the regulatory norms.

Colony counting within a culture plate involves many number of culture plate transport which includes moving culture plates from incubators to microscope plate and to storage back again. Manual counting of the bacteria colonies is difficult especially for a novice and hence, requires trained laboratory technician. Manual counting of the bacteria colonies is time consuming and involves relatively high labor costs. Additionally, the manual counting of colonies by the lab worker may also results in inaccurate counts of the bacteria colonies. For example, in some instances up to one thousand colonies can be counted and such colonies may be as small as 0.1 millimeters and spaced as close as 0.2 millimeters. As a result, such counting is extremely time consuming, inaccurate, laborious, and exceedingly costly both in time and required skilled labor. Typically, 80% of the petri-dish in a single batch does not have any colony growth. In an analog system, the microbiologist needs to analyze all the petri-dishes with or without colony growth which is time consuming and laborious resulting in fatigue to the lab technician.

Therefore, there exists a need for a device and a method for lighting, conditioning and capturing image(s) of organic sample(s), which obviates the aforementioned drawbacks.

SUMMARY

The principal object of embodiments herein is to provide a device for lighting, conditioning and capturing image(s) of organic sample(s).

Another object of embodiments herein is to provide a method of capturing image(s) of organic sample(s).

Another object of embodiments herein is to provide a device for automatic capturing of images of organic sample(s) cultivated on petri dish of different sizes.

Another object of embodiments herein is to provide a device which captures accurate image(s) of organic sample(s) such as but not limited to micro-organisms, where the device is configured for use in colony counting of micro-organisms.

Another object of embodiments herein is to provide a device for capturing images of organic sample(s) related to identification of microbial colonies present in the organic samples(s).

Another object of embodiments herein is to provide a device which has a fixed focus on organic sample(s) to facilitate capturing of accurate image(s) of organic sample(s) thereby enabling repeatability in quality of images captured by the device.

Another object of embodiments herein is to provide a color calibrated imaging device which provides diffused illumination by using polychromatic LED lights, light reflectors and light diffusers for optimal color reproduction of micro-biological colonies contained in organic sample(s).

Another object of embodiments herein is to provide a device for standardizing the imaging process by eliminating entrance of any ambient light by providing a closed photo compartment at all times thereby enhancing the quality of image captured by the device resulting in reliable colony counting.

Another object of embodiments herein is to provide a device in which the micro-organism colonies are illuminated in a calibrated light environment in the dome shaped light reflector which directs the reflection of light from the petri dish towards a digital camera.

Another object of embodiments herein is to provide a device with light diffusers which eliminates image noise so that only focused array of light is selected up by the a digital camera.

Another object of embodiments herein is to provide a device which is configured for automated entry and exit of the organic sample(s) for point accuracy.

Another object of embodiments herein is to provide a device which can capture images of organic sample in different lighting and color conditions thereby improving detection of microbiological colonies by increasing the contrast from the background medium.

Another object of embodiments herein is to provide a device which is adapted to sense the presence of the petri-dish inside a photo compartment and automatically triggers the scan acquisition control.

These and other objects of embodiments herein will be better appreciated and understood when considered in conjunction with following description and accompanying drawings. It should be understood, however, that the following descriptions, while indicating embodiments and numerous specific details thereof, are given by way of illustration and not of limitation. Many changes and modifications may be made within the scope of the embodiments herein without departing from the spirit thereof, and the embodiments herein include all such modifications.

BRIEF DESCRIPTION OF DRAWINGS

The embodiments are illustrated in the accompanying drawings, throughout which like reference letters indicate corresponding parts in various figures. The embodiments herein will be better understood from the following description with reference to the drawings, in which.

DETAILED DESCRIPTION

Figure 1:
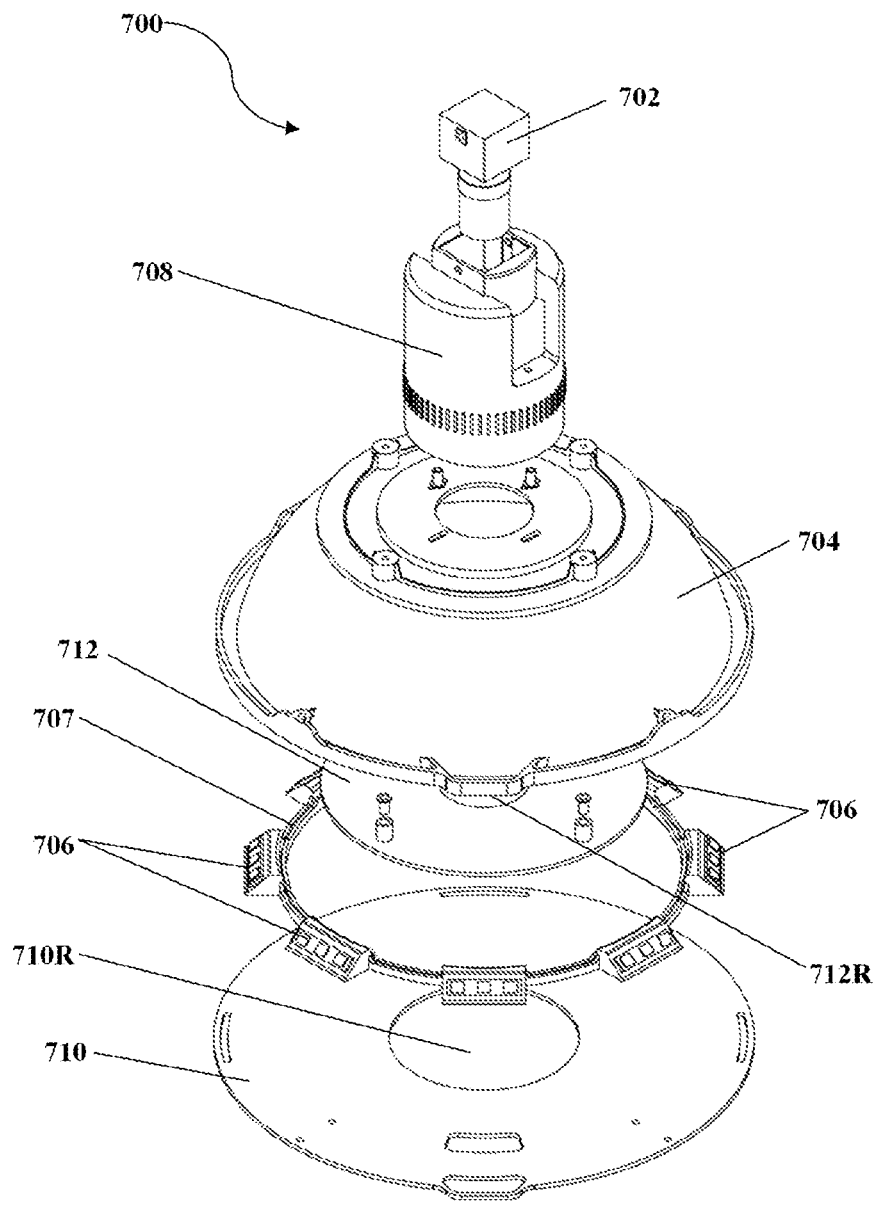
FIG. 1 depicts an exploded view of a device for lighting, conditioning and capturing image(s) of organic sample(s), according to embodiments as disclosed herein.

The embodiments herein and the various features and advantageous details thereof are explained more fully with reference to the non-limiting embodiments that are illustrated in the accompanying drawings and detailed in the following description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

The embodiments herein achieve a device and a method for lighting, conditioning and capturing images(s) of organic sample(s). Further, embodiments herein achieve the device which captures accurate image(s) of the organic sample(s). Referring now to the drawings FIGS. 1 through 4, where similar reference characters denote corresponding features consistently throughout the figures, there are shown embodiments.

Figure 2:
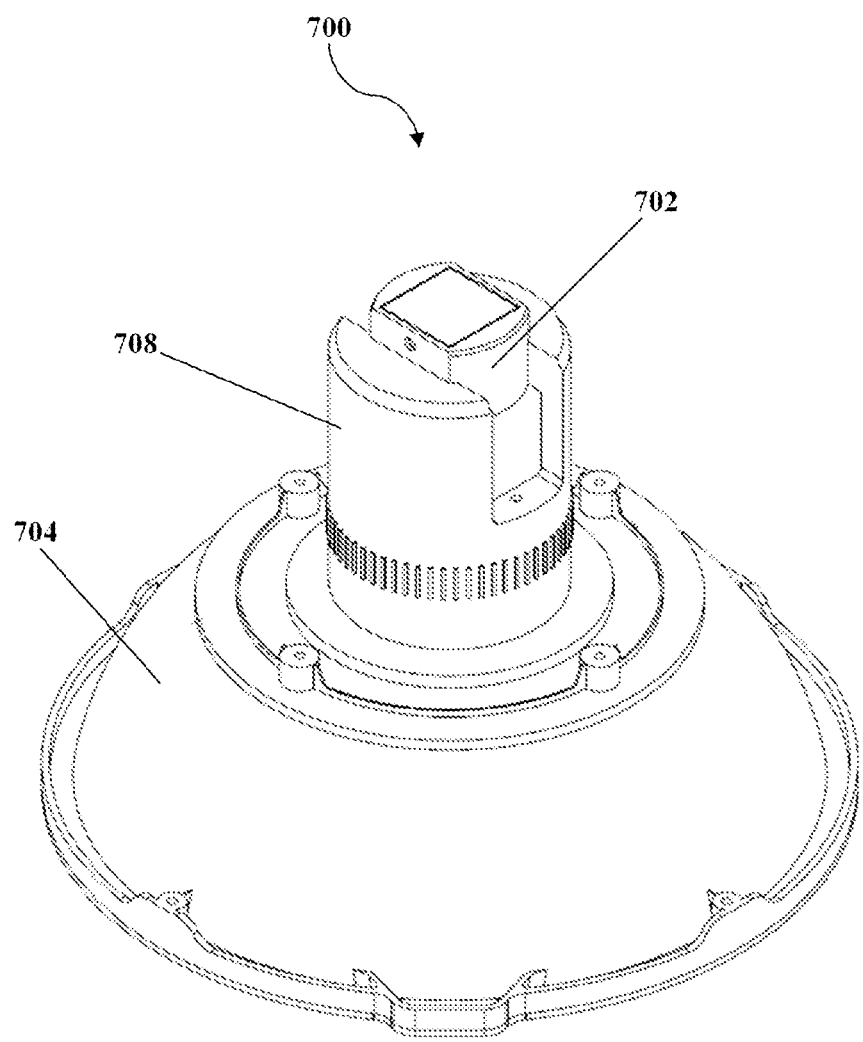
FIG. 2 depicts a perspective view of the device, according to embodiments as disclosed herein.

FIG. 1 depicts an exploded view of a device (700) for lighting, conditioning and capturing images(s) of organic sample(s), according to embodiments as disclosed herein. FIG. 2 depicts a perspective view of the device (700), according to embodiments as disclosed herein. In an embodiment, the device (700) includes an image capture device (702), a stationary light reflector (704), a plurality of lights (706), a light support ring (707), a holder (708), a first light diffuser (710) and a second light diffuser (712). For the purpose of this description and ease of understanding, the device (700) is explained herein with below reference to lighting, conditioning and capturing images(s) of organic sample(s) such as but not limited to micro-organisms for analyzing microbial growth cultivated on a petri dish thereby assisting in determining the type of micro-organisms present in the organic sample(s) and number of colonies present in each type of micro-organisms in a microbiological laboratory. However, it is also within the scope of the invention to use/practice the device (700) for lighting, conditioning and capturing image(s) or videos of any other organisms or blood samples or specimens or any other samples taken from any living things in any of a research laboratory, food or beverage industry, pharmaceutical industry or any other applications without otherwise deterring the intended function of the device (700) as can be deduced from the description and corresponding drawings.

The image capture device (702) is adapted to capture image(s) of the organic sample(s) based on input from an artificial intelligence (AI) based controller system (not shown). The image capture device (702) is disposed above the stationary light reflector (704). The image capture device (702) is mounted on the holder (708). The image capture device (702) is adapted to be moved to one of a plurality of positions in relation to the organic sample(s). For the purpose of this description and ease of understanding, the image capture device (702) is considered to be a camera. Examples of the image capture device (702) includes but not limited to digital camera, multispectral camera, charge coupled device (CCD) type camera, scanner, a thermal camera, an ultraviolet (UV) camera, near-infrared (NIR) camera and so on. However, it is also within the scope of the invention to use any other type of cameras for capturing the images of organic sample(s) without otherwise deterring the intended function of the image capture device (702) as can be deduced from the description and corresponding drawings. The image(s) captured by the image capture device (702) is transferred to the AI based controller system (not shown). The AI based controller system provides an output on type of micro-organism present in the organic sample(s) and number of colonies present in each type of micro-organism based on the image(s) captured by the image capture device (702). It is also within the scope of the invention to configure the image capture device (702) to capture and transfer videos of the organic sample(s) to the AI based controller system for determining the type of micro-organism present in the organic sample(s) and number of colonies present in each type of micro-organism. The AI based controller system provides the output type of micro-organism present in the organic sample(s) and number of colonies present in each type of micro-organism to a display screen or a user interface unit.

Figure 3:
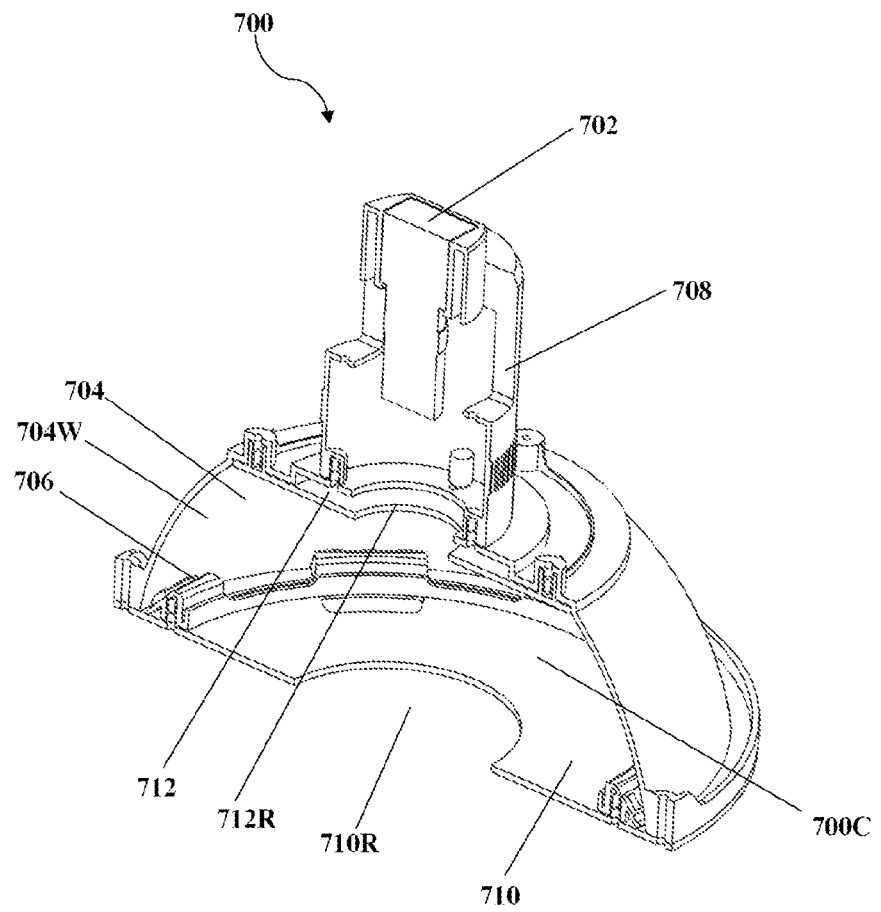
FIG. 3 depicts a cross-sectional view of the device, according to embodiments as disclosed herein.

In an embodiment, the stationary light reflector (704) is adapted to reflect the illumination of the lights (706) to facilitate uniform distribution of illumination to at least one of a photo compartment (700C), as shown in FIG. 3) and the organic sample(s). The stationary light reflector (704) is always stationary in relation to the organic sample(s). The stationary light reflector (704), the first light diffuser (710) and the second light diffuser (712) defines the photo compartment (700C). An entirety of inner portion of the stationary light reflector (704) is coated with white color. In an embodiment, the stationary light reflector (704) substantially defines a dome shape configuration. In another embodiment, at least one of an inner portion and an outer portion the stationary light reflector (704) defines a polygonal shape configuration. It is also within the scope of the invention to provide the stationary light reflector (704) in any other shape without otherwise deterring the intended function of the stationary light reflector (704) as can be deduced from the description and corresponding drawings.

In an embodiment, the plurality of lights (706) is adapted to focus an illumination onto the stationary light reflector (704). The plurality of lights (706) is provided within the stationary light reflector (704). The plurality of lights (706) comprises at least one red light, at least one green light and at least one blue light. Each light (706) is a LED light. Each light (706) is near to and facing an inner wall (704W), as shown in FIG. 3) of the stationary light reflector (704). The plurality of lights (706) is mounted on the light support ring (707). The lights (706) and the light support ring (707) are disposed on the first light diffuser (710), (as shown in FIG. 3). The plurality of lights (706) is positioned in a circular array (as shown in FIG. 1). The AI based controller system is adapted to control the illumination level of the lights (706) by altering the intensity of the lights (706).

The holder (708) is adapted to hold the image capture device (702). In an embodiment, the holder (708) is adapted to facilitate a change in focus of the image capture device (702). The holder (708) is mounted on the stationary light reflector (704).

In an embodiment, the first light diffuser (710) is adapted to diffuse the illumination of the lights (706) thereby reducing the reflection and glare of the illumination. The first light diffuser (710) defines at least one aperture (710R), as shown in FIG. 1 and FIG. 3) adapted to facilitate the image capture device (702) to capture image(s) of the organic sample therethrough. The organic sample cultivated on the petri dish is positioned below the aperture (710R) of the first light diffuser (710) and accordingly, the image capture device (702) captures images of the organic samples. The first light diffuser (710) is secured at a bottom end of the stationary light reflector (704). For example, the first light diffuser (710) is secured to the stationary light reflector (704) by using fasteners. It is also within the scope of the invention to secure the first light diffuser (710) to the stationary light reflector (704) by using any other temporary joint or permanent joint. The first light diffuser (710) is provided below and spaced away and opposite to the second light diffuser (712). At least a portion of the first light diffuser (710) which is facing the second light diffuser (712) is coated with matte black to diffuse the illumination of the lights (706) thereby reducing the reflection and glare of the illumination emitted by the lights (706).

In an embodiment, the second light diffuser (712) is adapted to diffuse the illumination of the lights (706) thereby reducing the reflection and glare of the illumination. The second light diffuser (712) defines at least one aperture (712R), as shown in FIG. 1 and FIG. 3) adapted to facilitate the image capture device (702) to capture image(s) of the organic sample there through. The second light diffuser (712) is provided below and spaced away from the image capture device (702). The second light diffuser (712) is provided above and spaced away from the first light diffuser (710). The second light diffuser (712) is parallel and co-axial and opposite to the first light diffuser (710). The second light diffuser (712) is secured at a top end of the stationary light reflector (704). For example, the second light diffuser (712) is secured to the stationary light reflector (704) by using fasteners. It is also within the scope of the invention to secure the second light diffuser (712) to the stationary light reflector (704) by using any other temporary joint or permanent joint. At least a portion of the second light diffuser (712) which is facing the first light diffuser (710) is coated with matte black to diffuse the illumination of the lights (706) thereby reducing the reflection and glare of the illumination emitted by the lights (706).

The conditioning of light is achieved by using the stationary light reflector (704) and the light diffusers (710, 712) thereby providing optimal lighting condition in the photo compartment (700C).

Figure 4:
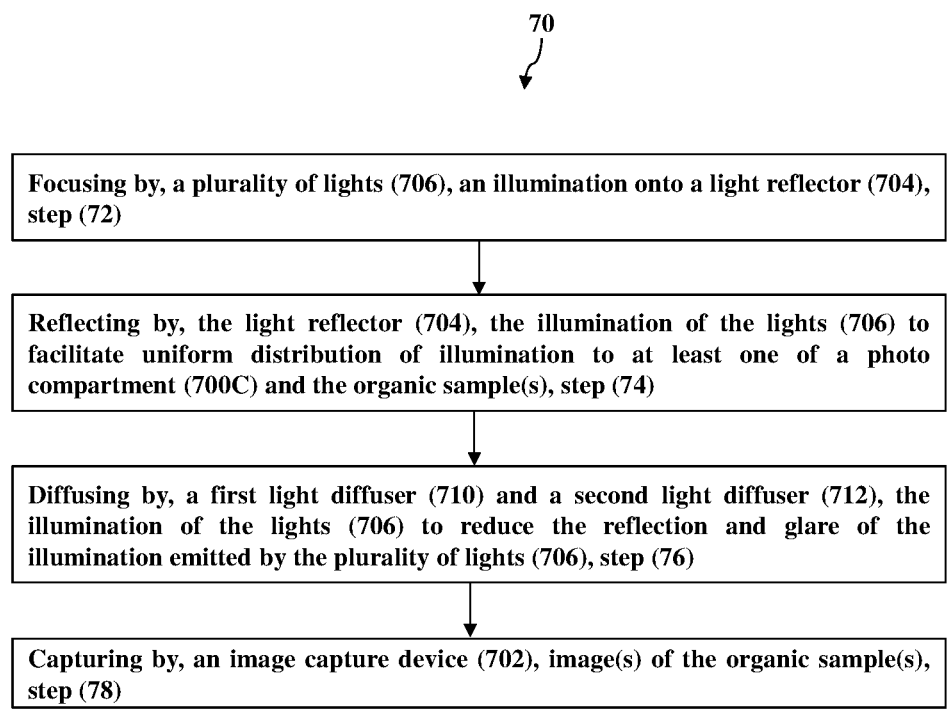
FIG. 4 depicts a flowchart indicating a method for lighting, conditioning and capturing images(s) of organic sample(s), according to embodiments as disclosed herein.

FIG. 4 depicts a flowchart indicating a method (70) for lighting, conditioning and capturing images(s) of organic sample(s), according to embodiments as disclosed herein. For the purpose of this description and ease of understanding, the method (70) is explained herein below with reference to lighting, conditioning and capturing images(s) of organic sample(s) such as but not limited to micro-organisms for analyzing microbial growth cultivated on a petri dish thereby assisting in determining the type of microorganisms present in the organic sample(s) and number of colonies present in each type of micro-organisms in a microbiological laboratory. However, it is also within the scope of this invention to practice/implement the entire steps of the method (70) in a same manner or in a different manner or with omission of at least one step to the method (70) or with any addition of at least one step to the method (70) for lighting, conditioning and capturing image(s) of any other organisms or blood samples or specimens or any other samples taken from any living things in any of a research laboratory, food or beverage industry, pharmaceutical industry and any other applications without otherwise deterring the intended function of the method (70) as can be deduced from the description and corresponding drawings. At step 72, the method (70) includes, focusing, by a plurality of lights (706), an illumination onto a stationary light reflector (704).

At step 74, the method (70) includes reflecting, by the stationary light reflector (704), the illumination of the lights (706) to facilitate uniform distribution of illumination to at least one of a photo compartment (700C) and the organic sample(s).

At step 76, the method (70) includes diffusing, by a first light diffuser (710) and a second light diffuser (712), the illumination of the lights (706) to reduce the reflection and glare of the illumination emitted by the plurality of lights (706).

At step 78, the method (70) includes, capturing, by an image capture device (702), image(s) of the organic sample(s).

The method (70) includes activating, by an artificial intelligence (AI) based controller system, the image capture device (702) to capture image(s) of the organic sample(s).

The method (70) includes controlling, by the AI based controller system, the illumination level of the lights (706) by altering the intensity of illumination from the lights (706).

Further, the method (70) comprises, transferring the captured image(s) of organic sample from the image capture device (702) to the AI based controller system.

Further, the method (70) comprises, providing, by the AI based controller system, an output on type of micro-organism present in the organic sample(s) and number of colonies present in each type of micro-organism based on the image(s) captured by the image capture device (702).

The method (70) includes positioning the organic sample(s) below at least one aperture (710R) of the first light diffuser (710).

Further, the method (70) comprises, moving the image capture device (702) to one of a plurality of positions in relation to the organic sample(s) by changing a focus of the image capture device (702) through a holder (708), where the holder (708) is adapted to hold the image capture device (702).

The technical advantages of the device (700) are as follows. The device is adapted for automatic capturing of images of organic sample(s) of different sizes. The device is adapted to capture accurate image(s) of organic sample(s). The device which has a fixed focus on organic sample(s) to facilitate capturing of accurate image(s) of organic sample(s) thereby enabling repeatability in quality of images captured by the device. The device is a color calibrated imaging device which provides diffused illumination by using polychromatic LED lights, light reflectors and light diffusers for optimal color reproduction of micro-biological colonies contained in organic sample(s). The device is adapted for standardizing the imaging process by eliminating entrance of any ambient light by providing a closed photo compartment at all times thereby enhancing the quality of image captured by the device resulting in reliable colony counting. The device is adapted to capture images of organic sample in different lighting and color conditions thereby improving detection of microbiological colonies by increasing the contrast from the background medium. The device is configured for automated entry and exit of the organic sample(s) for point accuracy. The device is adapted to sense the presence of the petri-dish inside the photo compartment and automatically triggers the scan acquisition control. The micro-organism colonies are illuminated in a calibrated light environment in the dome shaped light reflector which directs the reflection of light from the petri dish towards a digital camera. The device is adapted to eliminate image noise so that only focused array of light is selected up by the digital camera.

The foregoing description of the specific embodiments will so fully reveal the general nature of the embodiments herein that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of embodiments, those skilled in the art will recognize that the embodiments herein can be practiced with modifications within the spirit and scope of the embodiments as described herein.

We claim:

1. A device for lighting, conditioning and capturing image(s) of organic sample(s), comprising:
   a stationary light reflector, the stationary light reflector is always stationary in relation to the organic sample(s);
   a plurality of lights disposed within the stationary light reflector;
   an image capture device disposed above the stationary light reflector, wherein: the plurality of lights is adapted to focus an illumination onto the stationary light reflector; the stationary light reflector is adapted to reflect the illumination of the lights to facilitate uniform distribution of illumination to at least one of a photo compartment and the organic sample(s); and the image capture device is adapted to capture image(s) of the organic sample(s);
   a first light diffuser adapted to diffuse the illumination of the lights thereby reducing the reflection and glare of the illumination of the lights, wherein the first light diffuser defines at least one aperture adapted to facilitate the image capture device to capture image(s) of the organic sample therethrough; the organic sample(s) is positioned below the at least one aperture of the first light diffuser; the image capture device is adapted to be moved to one of a plurality of positions in relation to the organic sample(s); and an inner portion of the light reflector is coated with white color;
   a second light diffuser adapted to diffuse the illumination of the lights thereby reducing the reflection and glare of the illumination of the lights, wherein: the second light diffuser defines at least one aperture adapted to facilitate the image capture device to capture image(s) of the organic sample(s) there through; the stationary light reflector and the light diffusers are adapted to condition the illumination of the lights; the second light diffuser is provided below and spaced away from the image capture device; the second light diffuser is provided above and spaced away from the first light diffuser; and at least a portion of the second light diffuser which is facing the first light diffuser is coated with matte black to diffuse the illumination of the lights thereby reducing the reflection and glare of the illumination of the lights.

2. The device of claim 1, wherein
   at least a portion of the first light diffuser which is facing the second light diffuser is coated with matte black to diffuse the illumination of the lights thereby reducing the reflection and glare of the illumination of the lights;
   the second light diffuser is secured at a top end of the stationary light reflector;
   the first light diffuser is secured at a bottom end of the stationary light reflector;
   the second light diffuser is parallel and co-axial and opposite to the first light diffuser;
   the stationary light reflector, the first light diffuser and the second light diffuser defines the photo compartment; and
   the photo compartment is a closed photo compartment at all times.

3. The device of claim 1, wherein the device comprises a holder adapted to hold the image capture device, wherein the holder is adapted to facilitate a change in focus of the image capture device;
   the image capture device is disposed above the stationary light reflector;
   at least one of an inner portion and an outer portion the stationary light reflector defines a polygonal shape configuration;
   the image capture device is at least a camera;
   the plurality of lights is provided within the stationary light reflector;
   the plurality of lights comprises at least one red light, at least one green light and at least one blue light; and
   each light of the plurality of lights is a LED light.

4. The device of claim 3, wherein the device comprises a light support ring adapted to mount the plurality of lights, wherein each light of the plurality of lights is near to and facing an inner wall of the stationary light reflector;
   each light of the plurality of lights is spaced away from the other light;
   the plurality of lights are positioned in a circular array; and
   the plurality of lights and the light support ring are disposed on first light diffuser.

5. The device of claim 1, wherein the stationary light reflector substantially defines a dome shape configuration;
   the image capture device is adapted to capture image(s) of the organic sample(s) based on input from an artificial intelligence (AI) based controller system;
   the image(s) captured by the image capture device is sent to the artificial intelligence (AI) based controller system; and
   the AI based controller system provides an output on type of microorganisms present in the organic sample(s) and number of colonies present in each type of microorganisms based on the image(s) captured by the image capture device.

6. A method for lighting, conditioning, and capturing image(s) of an organic sample(s), comprising:
   focusing by, a plurality of lights, an illumination onto a stationary light reflector;

reflecting by, the stationary light reflector, the illumination of the lights to facilitate uniform distribution of illumination to at least one of a photo compartment and the organic sample(s);

diffusing by, a first light diffuser and a second light diffuser, the illumination of the lights to reduce the reflection and glare of the illumination by the plurality of lights, capturing by, an image capture device, image(s) of the organic sample(s);

positioning the organic sample(s) below at least one aperture of the first light diffuser;

moving the image capture device to one of a plurality of positions in relation to the organic sample(s) by changing a focus of the image capture device through a holder, where the holder is adapted to hold the image capture device, wherein:

- at least a portion of the first light diffuser which is facing the second light diffuser is coated with matte black to diffuse the illumination of the lights thereby reducing the reflection and glare of the illumination of the lights;
- at least a portion of the second light diffuser which is facing the first light diffuser is coated with matte black to diffuse the illumination of the lights thereby reducing the reflection and glare of the illumination of the lights;
- an inner portion of the stationary light reflector is coated with white color;
- the stationary light reflector substantially defines a dome shape configuration, where the stationary light reflector is always stationary in relation to the organic sample(s);
- each light is near to and facing an inner wall of the stationary light reflector;
- the plurality of lights are mounted on a light support ring, where the plurality of lights are positioned in a circular array;
- the second light diffuser is provided below and spaced away from the image capture device;
- the second light diffuser is provided above and spaced away from the first light diffuser;
- the image capture device is disposed above the stationary light reflector;
- the image capture device is at least a camera;
- the plurality of lights is provided within the stationary light reflector;
- the second light diffuser is parallel and co-axial and opposite to the first light diffuser;
- the stationary light reflector, the first light diffuser and the second light diffuser defines the photo compartment;
- the second light diffuser defines at least one aperture adapted to facilitate the image capture device to capture image(s) of the organic sample(s) therethrough; and
- the at least one aperture of the first light diffuser is adapted to facilitate the image capture device to capture image(s) of the organic sample therethrough.

7. The method of claim 6, further comprising:

activating, by an artificial intelligence (AI) based controller system, the image capture device to capture image(s) of the organic sample(s);

controlling, by the AI based controller system, the illumination level of the lights by altering the intensity of illumination from the lights;

transferring the captured image(s) of organic sample(s) from the image capture device to the artificial intelligence (AI) based controller system; and providing, by the AI based controller system, an output on type of microorganisms present in the organic sample(s) and number of colonies present in each type of micro-organisms based on the image(s) captured by the image capture device.

* * * * *